United States Patent [19]

Mori et al.

[11] 4,180,588

[45] Dec. 25, 1979

[54] IMMUNOSUPPRESSANT

[75] Inventors: Takenori Mori, Takarazuka; Haruhisa Shirahama, Sapporo; Tadashi Kurokawa, Sendai, all of Japan

[73] Assignee: Mitsubishi Chemical Industries, Ltd., Tokyo, Japan

[21] Appl. No.: 881,238

[22] Filed: Feb. 27, 1978

[30] Foreign Application Priority Data

Mar. 9, 1977 [JP] Japan .................................. 52/25698

[51] Int. Cl.$^2$ .......................................... A61K 31/195
[52] U.S. Cl. ..................................................... 424/319
[58] Field of Search ......................................... 424/319

[56] References Cited

PUBLICATIONS

Jadot et al., Biochim. Biophys.Acta. vol. 43, pp. 322–328 (1960).

Weaver et al., J. Biol. Chem., Vol. 246, No. 7 pp. 2010–2014 (1971).

*Primary Examiner*—Leonard Schenkman
*Attorney, Agent, or Firm*—Stevens, Davis, Miller & Mosher

[57] ABSTRACT

A pharmaceutical composition comprising an immunosuppressively effective amount of N-(p-hydroxyphenyl)-L-glutamine or the pharmaceutically acceptable acid addition salt thereof and a pharmaceutically acceptable adjuvant.

5 Claims, 2 Drawing Figures

IMMUNOSUPPRESSANT

BACKGROUND OF THE INVENTION

1. Field of the Invention

This invention relates to an immunosuppressant. More particularly, this invention relates to an immunosuppressant containing N-(p-hydroxyphenyl)-L-glutamine or the pharmaceutically acceptable acid addition salt thereof as an active ingredient.

2. Description of the Prior Art

Of many compounds that have been prepared that are potentially useful as immunosuppressants, only a very few have made their way into clinical use because of their high level of toxicity and their significant side effects to living bodies. Therefore, there is a continuing need for the development of an improved immunosuppressant.

SUMMARY OF THE INVENTION

An immunosuppressant containing N-(p-hydroxyphenyl)-L-glutamine or the pharmaceutically acceptable acid addition salt thereof as an active ingredient.

DETAILED DESCRIPTION OF THE INVENTION

N-(p-hydroxyphenyl)-L-glutamine is represented by the formula (I):

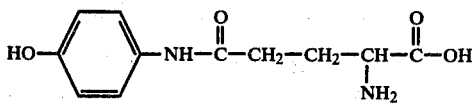

N-(p-hydroxyphenyl)-L-glutamine (I) of this invention forms acid addition salts with any of a variety of inorganic and organic acids.

The pharmaceutically acceptable acid addition salts of this invention can be obtained by reacting N-(p-hydroxyphenyl)-L-glutamine (I) with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toleune-sulfonic acid or the like.

N-(p-hydroxyphenyl)-L-glutamine, which is a known compound, can be prepared synthetically or isolated from the mushroom extract.

For example, synthesis of N-(p-hydroxyphenyl)-L-glutamine is described in J. Jadot et al., Biochim. Biophys. Acta, Vol. 43, P. 322 (1960) and R. F. Weaver et al., J. Biol. Chem., Vol. 246, P. 2010 (1971).

Extraction of N-(p-hydroxyphenyl)-L-glutamine from mushroom is described in R. F. Weaver et al., J. Biol. Chem., Vol. 246, P. 2010 (1971).

N-(p-hydroxyphenyl)-L-glutamine, when used as an immunosuppressant, may be administered alone or in combination with pharmaceutically acceptable carriers, the proportion of which is determined by the chosen route of administration and standard pharmaceutical practice.

The dosage administered will be dependent upon the age, health and weight of the recipient, the extent of the symptom, kind of concurrent treatment if any, frequency of treatment, and the nature of the effect desired. When the composition is administered orally, a larger quantity of the active agent will be required to produce the same effect as caused with a smaller quantity given parenterally.

Generally, a daily dosage of active ingredient compound will be from about 10 to 100 mg per kg of body weight parenterally, 50 to 500 mg per kg of body weight orally.

N-(p-hydroxyphenyl)-L-glutamine can be employed in dosage forms such as tablets, capsules, powder packets, granules, or liquid solutions, or elixirs, for oral administration, or sterile liquid formulations such as solutions or suspensions for parenteral use. Besides the active ingredient of this invention, the composition will contain a solid or liquid non-toxic pharmaceutical carrier for the active ingredient. In one embodiment of a composition, the solid carrier can be a capsule of the ordinary gelatin type. In another embodiment, the active ingredient can be tableted with or without adjuvants, or put into granules or powder packets. In this case, the suitable excipients which are used together include water; gelatin; saccharide such as lactose, glucose or the like; starch such as corn, wheat, rice, arrowroot starch or the like; stearates such as calcium stearate, magnesium stearate or the like; talc; vegetable oils; alcohols such as stearyl alcohol, benzyl alcohol or the like; gum; polyalkylene glycol and the like.

These capsules, tablets and powders will generally constitute from about 5% to about 100% and preferably from 25% to 100% by weight of active ingredient.

The pharmaceutical carrier can be a sterile liquid such as water and oils, including those of petroleum, animal, vegetable or synthetic origin, such as peanut oil, soybean oil, mineral oil, sesame oil, and the like.

In general, water saline, aqueous dextrose and related sugar solutions, and glycols such as ethylene glycol, and polyethylene glycol are preferred liquid carriers.

N-(p-hydroxyphenyl)-L-glutamine may be injected parenterally, that is, intramuscularly, intravenously or subcutaneously.

For parenteral administration, the compounds may be used in the form of sterile solutions containing other solutes, for example, sufficient saline or glucose to make the solution isotonic.

Suitable solvents for parenteral administration include sterile water, a solution of lidocaine hydrochloride (for intramuscular injection), saline solution, a glucose solution, a liquid for intravenous injection, an electrolyte solution (for intravenous injection) and the like. In parenteral adminstration, the active ingredient normally will constitute from 0.5 to 10% by weight, preferably from 1 to 10% by weight.

Oral administration can be in a suitable suspension or syrup, in which the active ingredient normally will constitute from 0.5 to 10% by weight. The pharmaceutical carrier in such composition can be a watery vehicle such as a flavoring agent, a syrup or a pharmaceutical mucilage.

N-(p-hydroxyphenyl)-L-glutamine possessing immunosuppressive activity depresses the immune response in a patient and supports transplants of organs and skin.

The compound of this invention is also useful to alleviate autoimmune disease which is any pathological condition that results when specific antibody or antigen responsive lymphocytes and their target antigenic determinants carried by normal body components interact within the body. In addition, the compound of this invention is useful to meliorating such conditions as arthritis, which is a major immunoinflammatory disease.

BRIEF DESCRIPTION OF THE DRAWING

In FIG. 1, the X axis represents mean volume change in the right hind foot (ml), and Y axis represents time of treatment (day). Similarly.

Figure 1:
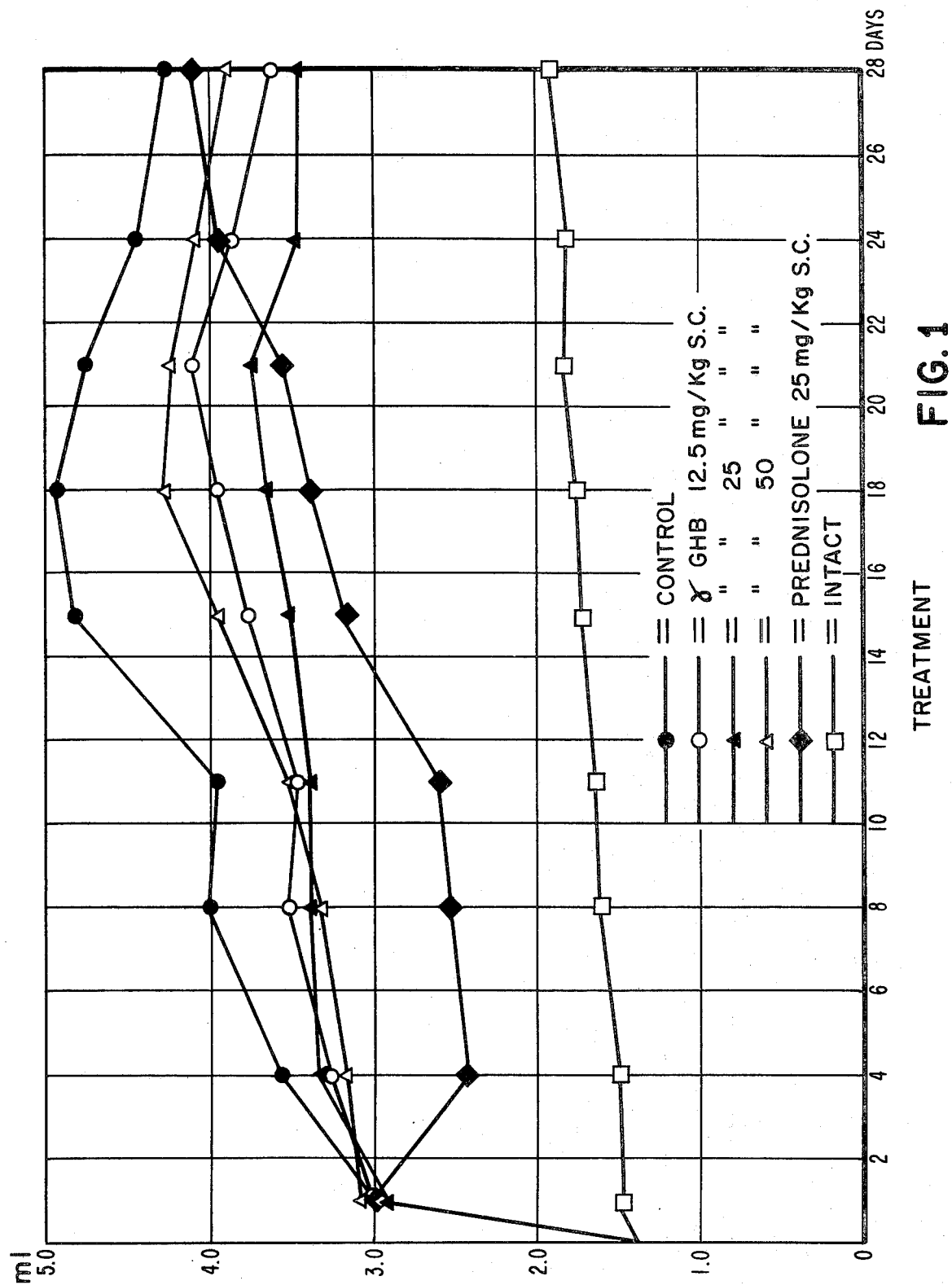
FIG. 1 illustrates changes with the passage of time in mean volumes of the Freund's adjuvant inflammed right hind foot of rats at various subcutaneous doses of N-(p-hydroxyphenyl)-L-glutamine or prednisolone.

Having generally described the invention, a more complete understanding can be obtained by reference to certain specific examples, which are included for purposes of illustration only and are not intended to be limiting unless otherwise specified.

REFERENCE EXAMPLE

Synthesis of N-(p-hydroxyphenyl)-L-glutamine

To 70 ml of an aqueous solution of 13.7 g of potassium bicarbonate and 10 g of methyl γ-L-glutamate, 12 ml of benzyloxycarbonyl chloride was added and the reaction mixture was stirred for 6 hr at room temperature, washed with 30 ml of ethyl ether to remove the excess of benzyloxycarbonyl chloride, and then acidified with 3N hydrochloric acid, resulting in turbid solution. The solution was then extracted with 150 ml of ethyl acetate. The organic layer was washed with 1 wt. % solution of potassium bicarbonate, and then evaporated to give the oily residue.

To the solution of the residue in 25 ml of methanol, 10 ml of 90 wt. % hydrazine hydrate was added dropwise over 5 to 10 minutes and the mixture was allowed to stand for 2 days a room temperature. After the removal of methanol, 60 ml of water was added to the residue to dissolve it and 6N hydrochloric acid was then added dropwise to pH 2, giving the precipitation. Subsequently saturated sodium acetate solution was added to pH 7 and the mixture was allowed to stand for an hour at 0° C. and the precipitate was collected by filtration. The crude product was recrystallized from water to give 7 g of pure N-benzyloxycarbonyl-γ-L-glutamohydrazide (mp; 175° to 176° C., yield; 33.5%).

To the solution of the hydrazide in 50 ml of 2.4N hydrochloric acid and 100 ml of ethyl acetate, 12 ml of aqueous 10 wt. % sodium nitrate solution was added over about fifteen minutes with stirring and cooling at 0° C.

After 30 minutes, the reaction mixture was extracted several times with ethyl acetate. To the combined organic layer, 3.5 g of p-hydroxyaniline dissolved in 100 ml of ethanol was added at once, and the resulting mixture was allowed to stand overnight at room temperature. The solvent was evaporated under reduced pressure to give the oily residue, which was extracted with several portions of methanol. To the combined methanol solution (300 ml), 4 ml of 50 vol. % acetic acid was added and then the solution was subjected to hydrogenolysis in the presence of 500 mg of 5 wt. % palladium-on-carbon catalyst. The removal of the catalyst by filtration followed by evaporation of the solvent gave the crystals, which were washed with methanol to remove the soluble impurities. The crude product was decolored with active carbon in water and then recrystallized from water, yielding 1.02 g (16.5%) of N-(p-hydroxyphenyl)-L-glutamine.

M.P.: 211°–212° C.

$[\alpha]_D^{23} = +33.0°$ (C=1.54, in 2N hydrochloric acid)

UV: $\lambda_{max}^{0.1\ N\ HCl}$ 246 nm, $\lambda_{max}^{H2O}$ 246 nm, $\lambda_{max}^{0.1\ N\ NaOH}$ 260 nm IR: $\nu_{OH}^{nujol}$ 3,270, 1,645, 1,610 cm$^{-1}$ NMR: $\delta_{NH3-D2O}^{DSS}$ 1.90 (m, 2H), 2.40 (m, 2H), 3.34 (t, 1H, J=6H$_z$), 6.14 (d, 2H, J=9H$_z$) 7.11 (d, 2H, J=9H$_z$)

MAS: m/e 238 (M$^+$), 201, 175, 109, 84

EXAMPLE 1

Inhibition of the blastogenesis of the human lymphocytes induced by phytohemagglutinin (PHA)

$1.5 \times 10^5$ human lymphocytes in RPMI-1 640 medium (produced by GIBCO) supplemented with 10 wt. % fetal calf serum were incubated with 0.1 μl of PHA and in the presence or absence of N-(p-hydroxyphenyl)-L-glutamine (total volume: 0.1 ml) in a CO$_2$ incubator at 37° C. for 72 hours. 0.1 μCi of $^3$H-thymidine was pulsed 7 hour before harvesting the cells. The lymphocytes were harvested and the radioactivity incorporated into the cells were counted. Table 1 shows the results of inhibitory effect of N-(p-hydroxyphenyl)-L-glutamine on the $^3$H-thymidine uptake by the lymphocytes stimulated by PHA.

Table 1

| Concentration of agent added (μ/ml) | % Inhibition |
|---|---|
| 40 | 99 |
| 4 | 67 |
| 0.4 | 27 |
| 0.04 | 14 |

As shown in the table, complete inhibition was observed at the concentration of 40 μg/ml of the compound. When 40 μg/ml of N-(p-hydroxyphenyl)-L-glutamine was added to the cell culture 0, 12, 24 and 48 hours after the PHA stimulation, almost complete inhibition were also observed in all cases.

EXAMPLE 2

Growth inhibition of tissue-culture cells $2.6 \times 10^5$/ml tissue culture cells (Daudi cells) derived from human lymphocytes in RPMI-1640 medium supplemented with 10% fetal calf serum were incubated with varied concentration of N-(p-hydroxyphenyl)-L-glutamine for 72 hours at 37° C. The number of live cells was determined by the trypane blue dye exclusion test. The results are given in Table 2.

Table 2

| Concentration (μg/ml) | Inhibition (%) (Control equals 100) |
|---|---|
| 0 (not added) | 100 |
| 4 | 100 |
| 40 | 11 |
| 400 | 0 |

It is clear from the above Table that the compound inhibited the growth of the tissue-culture cells by almost 90% at the concentration of 40 μg/ml.

The inhibitor effect gradually decreased as the time of addition of N-(p-hydroxyphenyl)-L-glutamine to the culture was delayed from 24 hours to 48 hours after the start of the incubation.

The incubation in the presence of N-(p-hydroxyphenyl)-L-glutamine for the first 24 hours in the whole incubation time of 72 hours did not exhibit any growth inhibition.

EXAMPLE 3

Prolongation of the skin allograft in rat Wister/MK rats received skin allografts from Fisher rats on day 0.

Recipient rats in the treatment group were administered intraperitoneally 25 mg/kg of N-(p-hydroxyphenyl)-L-glutamine dissolved in a phosphate buffer everyday from day -7 until the day on which the rejection was observed. Rats treated with the compound rejected their grafts in 15.0±1.7 days, while controls rejected in 9.0±1.6 days.

EXAMPLE 4

Effect of N-(p-hydroxyphenyl)-L-glutamine on the total number of nucleated cells and the plaque forming cells in the spleen The mice (ddY, 18 to 21 g) were intraperitoneally immunized with $1 \times 10^8$ sheep blood cells. The N-(p-hydroxyphenyl)-L-glutamine was administered subcutaneously on day 0, 1, 2 and 3. On day 4, the mice were sacrificed and the plaque forming cells in the spleen were determined according to the modified Cunningham's method (H. Fujiwara et al.; Experimental Method of Immunology Vol. 5, 1475 (1975)).

Total number of the nucleated cells in the spleen were counted after lysing erythrocytes with 0.5% acetic acid. The results are shown in Table 3.

Table 3

| Drug | No. of animals | PFC $\times 10^3$/spleen (No. of PFC ± S.E.) | Number of nucleated cells $\times 10^6$/spleen (No. of lymphocytes ± S.E.) |
|---|---|---|---|
| — | 4 | 163 ± 64 | 228 ± 18.8 |
| 6-Mercaptopurine (25 mg/kg) | 5 | 18.8 ± 7.9 | 78 ± 9.5 |
| N-(p-hydroxyphenyl)-L-glutamine (50 mg/kg) | 5 | 65.6 ± 9.5 | 176 ± 13.7 |
| N-(p-hydroxyphenyl)-L-glutamine (100 mg/kg) | 5 | 65.3 ± 14.0 | 226 ± 39.1 |

As shown in the above Table, 50 mg/kg of N-(p-hydroxyphenyl)-L-glutamine significantly inhibited the production of plaque forming cells, but did not affect the total number of the nucleated cells in the spleen.

EXAMPLE 5

Acute toxicity

The varied doses of N-(p-hydroxyphenyl)-L-glutamine in an aqueous 5% sodium carboxymethyl cellulose solution were intraperitoneally administered to the mice. The mortality 7 days after the administration was as follows:

| Dose | No. of dead mice/No. of treated mice |
|---|---|
| 10 g/kg | 1/1 |
| 5 g/kg | 2/5 |
| 3.535 g/kg | 1/5 |
| 2.5 g/kg | 0/5 |
| 1.768 g/kg | 0/5 |

Thus, $LD_{50}$ of N-(p-hydroxyphenyl)-L-glutamine was more than 5 g/kg.

EXAMPLE 6

Cytotoxic effect on the murine spleen cells $1 \times 10^6$/ml murine spleen cells in RPMI-1640 medium supplemented with 5% fetal calf serum were incubated with a varied concentration of N-(p-hydroxyphenyl)-L-glutamine for 48 hours at 37° C. And then the viability of the cells was determined by the trypane-blue dye exclusion test. The results are given in Table 4.

Table 4

| Concentration | Viability (%) |
|---|---|
| 0 | 86 |
| 10 | 83 |
| 100 | 87 |

It can be seen from the above Table that the compound did not exhibit any cytotoxic effect on the murine spleen cells within the range of the concentration tested.

EXAMPLE 7

Effect of N-(p-hydroxyphenyl)-L-glutamine on Adjuvant arthritis in rats

Sprague-Dawley rats weighing 150 to 180 g were randomized in 6 groups and kept in a controlled evironment for 2 weeks prior to use. They were fed a standard diet and were allowed to drink water freely ad libitum.

On day 0, each rat was injected in the planter region of the right hind paw with 0.05 ml Freund's Complete Adjuvant containing 6 mg/ml of heat killed *Mycobacterium butyricum* (Difco) in sterile paraffin oil.

The volume of the injected (right) and non-injected (left) feet up to a mark on the tibio-tarsal joint was measured by water over-flow method.

The sensitized rats were dosed subcutaneously from day 1 until day 21 with either 12.5, 25, or 50 mg/kg of N-(p-hydroxyphenyl)-L-glutamine (γ-GHB), 2.5 mg/kg of prednisolone, and vehicle for control group.

Mean volume changes in the right hind foot of rats are shown in FIG. 1, where ○, ▲, △, ◆, and □, represent those of the group treated with vehicle, 12.5, 25 and 50 mg/kg of N-(p-hydroxyphenyl)-L-glutamine, 2.5 mg/kg of prednisolone and intact, respectively.

Figure 2:
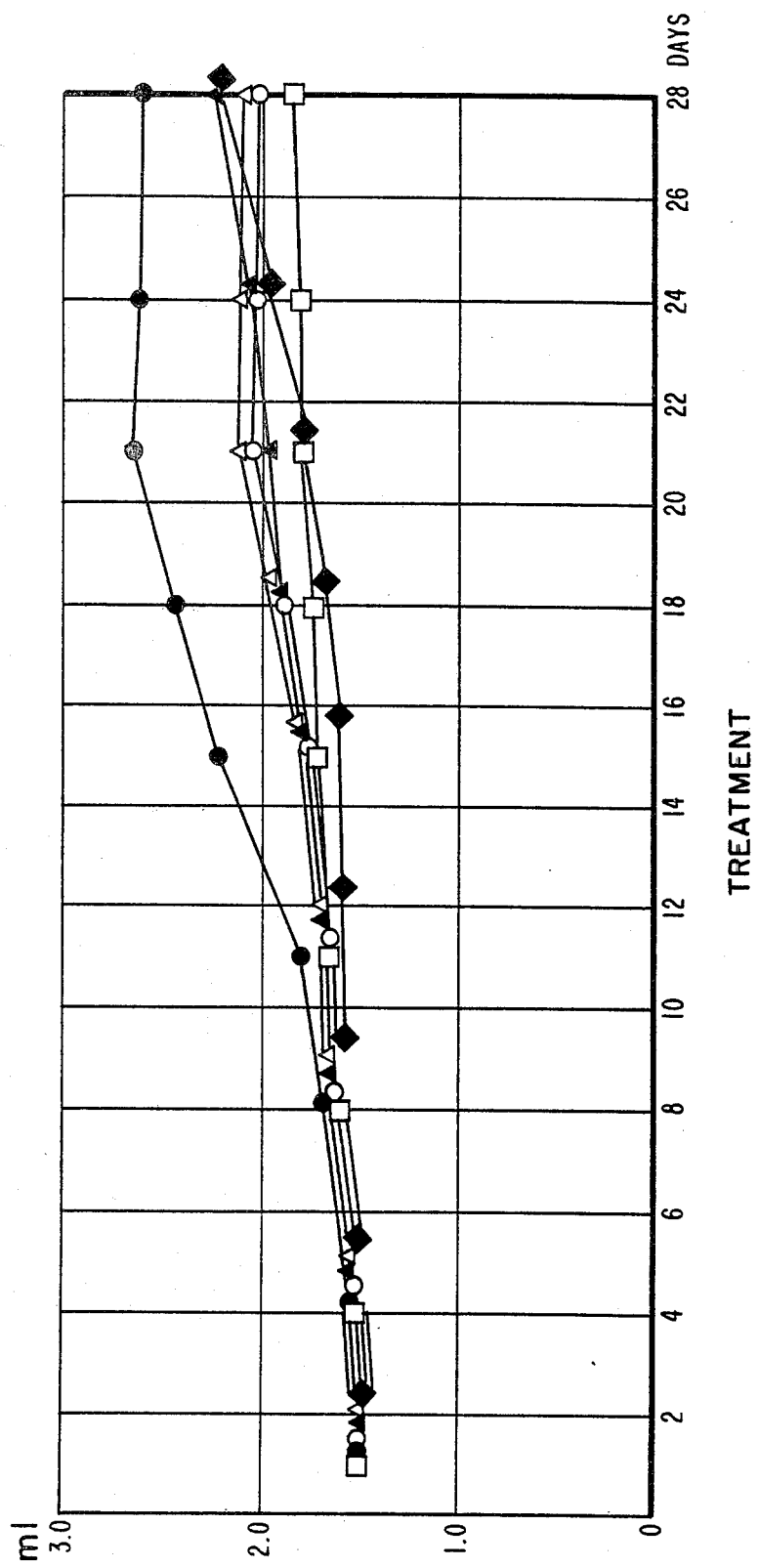
FIG. 2 illustrates mean volume changes in the non-injected left hind foot of rats.

FIG. 2 shows the mean volume changes in the left hind foot of rats, where the symbols are the same as in FIG. 1. As shown in FIG. 1 and FIG. 2, N-(p-hydroxyphenyl)-L-glutamine as well as prednisolone reduced significantly both left and right hind feet swelling.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A solid pharmaceutical composition in dosage unit form which comprises an immunosuppressively effective amount of N-(p-hydroxyphenyl)-L-glutamine or a pharmaceutically acceptable acid addition salt thereof and a pharmaceutically acceptable adjuvant.
2. A pharmaceutical composition of claim 1 in the form of an capsule.
3. A pharmaceutical composition of claim 1 in the form of a tablet.
4. A pharmaceutical composition of claim 1 in the form of a powder.
5. A method of suppressing the immune response in vivo, which comprises administering to a patient in need thereof a pharmaceutically effective amount of N-(p-hydroxyphenyl)-L-glutamine or a pharmaceutically acceptable acid addition salt thereof.

* * * * *